United States Patent [19]

Nakayama et al.

[11] Patent Number: 5,453,452

[45] Date of Patent: Sep. 26, 1995

[54] (METH)ACRYLATES, RESIN COMPOSITION USING THE SAME AND ULTRAVIOLET-CURING RESIN COMPOSITE FOR TRANSMISSION TYPE SCREENS

[75] Inventors: Kenji Nakayama, Omiya; Katsunori Shimura, Yono; Minoru Yokoshima, Toride; Nobuo Taniguchi, Urawa, all of Japan

[73] Assignee: Nippon Kayaku Kabushiki Kaisha, Tokyo, Japan

[21] Appl. No.: 168,674

[22] Filed: Dec. 16, 1993

Related U.S. Application Data

[62] Division of Ser. No. 897,436, Jun. 12, 1992, abandoned.

[30] Foreign Application Priority Data

| Jun. 21, 1991 | [JP] | Japan | 3-175730 |
| Jan. 10, 1992 | [JP] | Japan | 4-020726 |

[51] Int. Cl.⁶ .............. C08L 63/10; C08L 75/16; G02B 3/08
[52] U.S. Cl. .............. 522/92; 522/96; 522/103; 560/209; 560/221
[58] Field of Search .............. 560/209, 221; 522/96, 103, 92

[56] References Cited

U.S. PATENT DOCUMENTS

| 4,144,283 | 3/1979 | Matsubara | 560/221 |
| 4,745,137 | 5/1988 | Thomas et al. | 521/137 |
| 4,962,163 | 10/1990 | Hefner, Jr. et al. | 525/463 |
| 4,983,335 | 1/1991 | Matsuo et al. | 522/103 |
| 5,066,750 | 11/1991 | Hefner, Jr. et al. | 526/273 |
| 5,093,386 | 3/1992 | Bishop et al. | 522/103 |

FOREIGN PATENT DOCUMENTS

| 0126397 | 11/1984 | European Pat. Off. |
| 2230618 | 10/1990 | United Kingdom. |

OTHER PUBLICATIONS

Chemical Abstracts, vol. 93, 1980, Columbus, Ohio, US; abstract No. 26926b. B. Bresci et al., p. 8 "Order in polymers with biphenyl residues in the side-groups".

*Primary Examiner*—Susan W. Berman
*Attorney, Agent, or Firm*—Nields & Lemack

[57] ABSTRACT

This invention relates to (meth)acrylates represented by formula (1):

wherein, $R_1$ and $R_2$ are each independently H or $CH_3$ and average value of n is 1–5; resin composite comprising (A) an urethane (meth)acrylate and/or epoxy (meth)acrylate, (B) a (meth)acrylate represented by formula (1) above, (C) an ethylenically unsaturated compound other than component (A) or (B), and (D) a photopolymerization initiator; and cured products of said resin composites. The cured products of said resin composites of this invention have high refractive index and are superior in mold release property, shape reproducibility, restorability, and scratch resistance and suited in particular for transmission type screens.

2 Claims, No Drawings

(METH)ACRYLATES, RESIN COMPOSITION USING THE SAME AND ULTRAVIOLET-CURING RESIN COMPOSITE FOR TRANSMISSION TYPE SCREENS

This application is a Division of application Ser. No. 07/897,436, filed Jun. 12, 1992, now abandoned.

This invention relates to novel (meth)acrylates, which are useful as components for ultraviolet- or electron beam-curing resin composites, or more specifically as components for resin composites for lens and light-controlling films, resin composites using said esters, and in particular ultraviolet-curing resin composites suitable for transmission type screen such as Fresnel lens and lenticular lens used in video projectors and projection televisions and cured products of said resins.

Such types of lens have, heretofore, been formed by methods such as pressing and casting. The former has low productivity, since production by pressing is done through a cycle of heating, pressing and cooling. The latter requires long production time and high cost, since in casting, monomer is poured into metal molds and polymerized, and large number of molds are required. In order to solve such problems use of ultraviolet-curing resin composites have been variously proposed (see e.g. GB2230618).

By using such ultraviolet-curing resin composites, a method to produce transmission type screen has been successful to some extent. But there has been no proposal to meet the requirements of thin types such as projection television.

In order to solve the above described problem, the inventors of this invention have, as a result of ardent endeavor, discovered (meth)acrylates which have less smell, high curing speed by ultraviolet, and high refractive index and give soft cured products, and resin composites using said (meth)acrylate and completed this invention.

That is, this invention relates to:

(1) (meth)acrylates represented by formula (1)

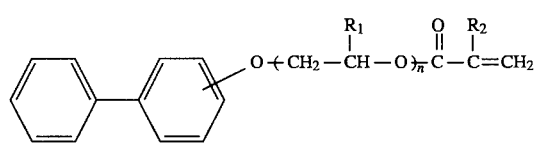

wherein, $R_1$ and $R_2$ are each independently H or $CH_3$, and average value of n is 1–5, (2) (meth)acrylate described in paragraph (1), represented by formula (2)

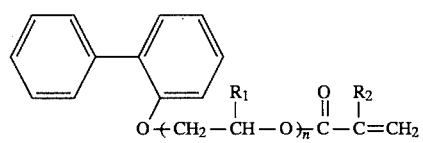

wherein, $R_1$ and $R_2$ are each independently H or $CH_3$, and average value of n is 1–5, (3) (meth)acrylate described in paragraph (1), represented by formula (3)

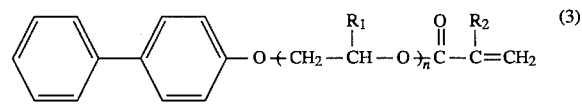

wherein, $R_1$ and $R_2$ are each independently H or $CH_3$, and average value of n is 1–5, (4) (meth)acrylate described in paragraph (1), represented by formula (4)

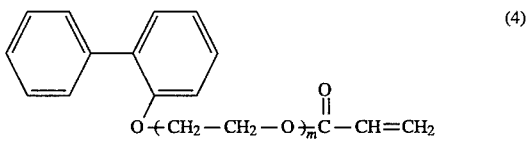

wherein, average value of m is 1–4, (5) resin composites characterized by containing; (A) urethane (meth)acrylate and/or epoxy (meth)acrylate, (B) (meth)acrylate represented by formula (1) described in paragraph (1), (C) ethylenically unsaturated compound other than (A) or (B), and (D) photopolymerization initiator, (6) resin composites described in paragraph (5), wherein (B) (meth)acrylate is a compound represented by formula (2) described in paragraph (2), (7) resin composites described in paragraph (5), wherein (B) (meth)acrylate is a compound represented by formula (3) described in paragraph (3), (8) resin composites described in paragraph (5), wherein (B) (meth)acrylate is a compound represented by formula (4) described in paragraph (4), (9) cured products of resin composites described in paragraph (5), (6), (7), or (8),

(10) ultraviolet-curing resin composites for transmission screen, comprising resin composites described in paragraph (5), (6), (7) or (8),

(11) cured products of ultraviolet curing resin composites for transmission screens described in paragraph (10).

The (B) novel (meth)acrylate of this invention represented by formula (1) can be prepared by reacting a compound represented by formula (5),

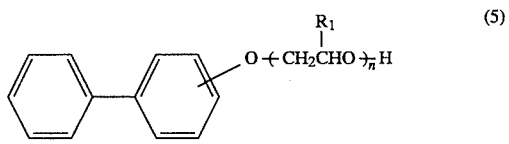

wherein, $R_1$ is H or $CH_3$ and average value of n is 1–5, with (meth)acrylic acid. The compounds represented by formula (5) are products formed, for example, by reaction between p-phenylphenol, o-phenylphenol or m-phenylphenol and ethylene oxide or propylene oxide. These products are readily available at the market. For example, there are Sanyo Chemical's product Newpol OPE-10 (product of reaction between 1 mol of o-phenylphenol and 1 mol of ethylene oxide), Newpol OPE-20 (product of reaction between 1 mol of o-phenylphenol and 2 mol of ethylene oxide), and Newpol OPE-40 (product of reaction between 1 mol of o-phenylphenol and 4 mol of ethylene oxide).

The reaction between compounds represented by formula (5) and (meth)acrylic acid can be carried out in the presence of esterification catalyst such as p-toluenesulfonic acid or sulfuric acid and polymerization inhibitor such as hydroquinone, phenothiazine or methylhydroquinone, preferably under presence of solvent (for example toluene, benzene, cyclohexane, n-hexane, n-heptane and others), and preferably at temperature of 70°–150° C. The amount of (meth)acrylic acid to be used per mol of compounds represented by formula (5) is normally 1–5 mol, preferably 1.05–2 mol. Esterification catalyst is added at concentration of normally 0.1–15 mol %, preferably 1–6 mol % based on (meth)acrylic acid used.

(Meth)acrylate of this invention have little smell and high refractive index, and when used as component of ultraviolet- or electron beam-curing resin composite, provides soft cured product.

The resin composites of this invention use (A) urethane (meth)acrylate and/or epoxy (meth)acrylate. As actual examples of urethane (meth)acrylates, reaction products of polyols such as ethylene glycol, 1,4-butanediol, neopentyl glycol, polycaprolactone-polyol, polyester-polyol, polycarbonate-diol, polytetramethylene-glycol, organic polyisocyanates such as hexamethylendiisocyanate, isoholon-diisocyanate, tolylenediisocyanete, xylylenediisocyanate, 4-4'-diphenylmethanediisocyanate and hydroxyl group-containing ethylenically unsaturated compounds such as 2-hydroxyethyl (meth)acrylate, 2-hydroxypropyl (meth)acrylate, 1,4-butanediol mono(meth)acrylate, ε-caprolactone addition product of 2-hydroxyethyl (meth)acrylate, pentaerythrytol tri(meth)acrylate, can be mentioned. The above described urethane (meth)acrylate can be obtained by preparing urethane oligomer by reacting preferably 1.1–2.0 equivalent of isocyanate group of the organic polyisocyanates with 1 equivalent of hydroxyl group of polyols at preferably 70°–90° C., followed by reacting preferably 1–1.5 equivalent of hydroxyl group of the hydroxyl group-containing ethylenically unsaturated compounds with 1 equivalent of isocyanate group of the urethane oligomer at preferably 70°–90° C. As preferable urethane (meth)acrylate, polyester-urethane acrylate, polycaprolactone-urethane acrylate, polytetramethylene-urethane acrylate may be given.

The number average molecular weight of urethane (meth)acrylate used in this invention is preferably 500–10,000.

As concrete examples of epoxy (meth)acrylate, reaction products of epoxy resins such as bisphenol A-type epoxy resin, bisphenol F-type epoxy resin, phenolnovolac-type epoxy resin, glycidyl-end-ether of bisphenol A-type propylen oxide addition product and fluorene-epoxy resin with (meth)acrylic acid may be given. The reaction of epoxy resins and (meth)acrylic acid is carried out at the ratio of preferably 0.8–1.5 equivalent, most preferably 0.9–1.1 equivalent of (meth)acrylic acid with 1 equivalent of epoxy group of the epoxy resins, using photopolymerizing vinyl monomer such as 2-hydroxyethyl (meth)acrylate, 2-hydroxylbutyl (meth)acrylate, trimetylolpropane tri(meth)acrylate, acryloylmorphorine, N-vinylpyrolidone, (meth)acrylic ester of phenyl glycidyl ether, phenoxyethyl (meth)acrylate, isobornyl (meth)acrylate, dicyclopentanyl (meth)acrylate as diluent during the reaction, preferably using catalyst (for example, benzyldimethylamine, triethylamine, benzyltrimethylammonium chloride, benzyltriethylammonium bromide, triphenylstibine) to accelerate the reaction. Amount of said catalyst used is preferably 0.1–10 wt. %, most preferably 0.3–5 wt. % based on the reaction mixture.

It is preferable to use polymerization inhibitor (for example, methoquinone, hydroquinone, phenothiazine) to prevent polymerization during reaction. The amount of use is preferably 0.01–1 wt. %, more preferably 0.05–0.5 wt. % based on the reaction mixture. The reaction temperature is preferably 60°–150° C., more preferably 80°–120° C. Bisphenol A-type epoxy acrylate and bisphenol F-type epoxy acrylate may be given as preferred epoxy (meth)acrylate.

The number average molecular weight of epoxy (meth)acrylate used in this invention is preferably 400–5,000.

(B) (Meth)acrylate of the resin composite of this invention can be any compound represented by above described formula (1), but the compounds especially preferred are compounds represented by above described formula (4).

As concrete examples of (C) ethylenically unsaturated compounds, which are component used in resin composite of this invention other than the (A) or (B), for example, N-vinyl-caprolactam, acryloylmorphorine, 2-hydroxypropyl (meth)acrylate, tetrahydrofurfuryl (meth)acrylate, phenoxyethyl (meth)acrylate, phenylglycidyl-ether (meth)acrylate, isobornyl (meth)acrylate, tribromophenyl (meth)acrylate, tribromobenzyl (meth)acrylate, tribromo-phenyloxyethyl (meth)acrylate, dibromophenyl-glycidyl-ether (meth)acrylate, dicyclopentanyl (meth)acrylate, polyethoxy di(meth)acrylate of tetrabromobisphenol A, tetraethoxy di(meth)acrylate of bisphenol A, tetraethoxy di(meth)acrylate of bisphenol F, tricyclodecanedimethylol di(meth)acrylate, di(meth)acrylate of ε-caprolactone addition product of neopentyl glycol hydroxypivalinate may be given. Preferred (C) ethylenically unsaturated compounds are phenoxyethyl acrylate, dicyclopentanyl acrylate, isobornyl acrylate, acrylic ester of phenyl glycidyl ether, tribromophenyl methacrylate, tribromophenyloxyethyl acrylate, tetraethoxy diacrylate of bisphenol A.

As (D) photopolymerization initiators, for example, copolymerizing photopolymerization initiators such as

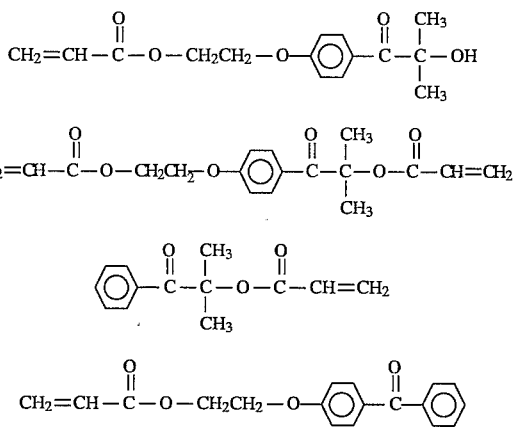

and benzoin, benzoin methy ether, benzoin isopropyl ether, acetophenone, 2,2-dimethoxy-2-phenylacetophenone, 2,2-diethoxy-2-phenylacetophenone, 1,1-dichloroacetophenone, 1-hydroxycyclohexyl phenyl ketone, 2-hydroxy- 2-methyl-1-phenyl-propane-1-one, 2-methyl-1-[4-(methylthio)phenyl] -2-morpholino-propane-1-one, N,N-dimethylaminoacetophenone, 2-methyl-anthraquinone, 2-ethylanthraquinone, 2-tert-butylanthra-quinone, 1-chloroanthraquinone, 2-amylanthraquinone, 2-aminoanthraquinone, 2,4-demethylthioxanthone, 2,4-diethylthioxantone, 2,4-diisopropylthioxantone, acetophenone dimethylketal, benzophenone, methylbenzophenone, 4,4'-dichlorobenzophenone, 4,4'-bis-diethylaminobenzophenone, Michler's ketone may be given. These may be used alone or as mixture of two or more.

As especially preferred (D) photopolymerization initiators, 1-hydroxycyclohexyl phenyl ketone, 2-hydroxy- 2-methyl-1-phenylpropane-1-one may be mentioned.

Moreover, these (D) photopolymerization initiators may be used in combination with one or two or more publicly known and conventionally used photo sensitizers such as ethyl ester of N,N-dimethylaminobenzoic acid, iso-amyl ester of N,N-dimethylaminobenzoic acid, triethanolamine, and triethylamine.

Preferred ratio of the components used for the resin composite of this invention is, (A) urethane (meth)acrylate and/or epoxy (metha)acrylate 10–50 wt. %, (B) (meth)acrylate 10–40 wt. %, (C) ethylenically unsaturated compound 10–70 wt. % and (D) photopolymerization initiator 0.1–10 wt. %.

In the resin composite of this invention, in addition to above described components, mold release agent, antifoaming agent, leveling agent, photostabilizer (for example, hindered amine), antioxidant, polymerization inhibitor, and antistatic agent may be used.

The resin composite of this invention can be prepared by mixing and dissolving all the components.

The resin composite of this invention is especially useful in transmission screen such as Fresnel lens and lenticular lens, but it is also useful in various coating agent, potting agent and adhesives.

Cured product of the resin composite of this invention can be obtained by curing by ultraviolet irradiation conventional methods. Actually, the resin composite of this invention is applied onto, for example, a stamper with a shape of Fresnel lens or lenticular lens, to form a layer of said resin composite, hard transparent base board is placed on the layer, at this configuration ultraviolet light is irradiated on the said hard transparent base board side by high voltage mercury lamp or others to cure said resin composite, and removed from said stamper. In this manner, soft transmission type screen such as Fresnel lens or lenticular lens of refractive index (23° C.) of normally 1.55 or above, under preferable conditions of 1.56 or above can be obtained.

In the following, this invention will be more concretely explained by examples and applied examples. Evaluations in the applied examples were carried out as follows. "Part" in the examples means part by weight.

(1) Release properties from mold: Ease of removal of cured resin from mold.
  ○ Removed from mold easily
  Δ Removed from mold with some difficulty
  X Difficult to remove or stuck residue on mold (2) Shape reproducibility: Surface feature of cured ultraviolet curing resin and surface feature of metal mold are observed.
  ○ Good reproducibility
  X Poor reproducibility (3) Restorability: Finger nail is pressed on the surface, which was facing the metal mold, of the cured ultraviolet-curing resin and the surface was observed after allowed to stand for 30 minutes.
  ○ Scar of nail pressing not observed
  Δ Slight scar faintly visible
  X Scar remaining.

(4) Refractive index (23° C.): Measurement of refractive index (23° C.) of cured ultraviolet curing resin.

(5) Scratch resistance: On the surface, which was facing the metal mold, of the cured ultraviolet-curing resin, an acrylic plate (width 15 mm, length 100 mm, thickness 2 mm) is vertically pressed on strongly, and the plate is moved between a distance of 100 mm at a speed of one go-and-back movement per second and ten back-and-forth movements are made. The scratches on the surface are observed.
  ○○ No scratches observed
  ○ A few line scars are observed
  Δ Partial belt shape scars observed
  X Belt shape scars on whole test area Synthesis example of (A) urethane (meth)acrylate
Synthesis example 1
120 parts of polyesterdiol (polyesterdiol of neopentyl glycol and adipic acid, molecular weight 2,000, OH value 56.1), 2.48 parts of ethylene glycol. 34.8 parts of tolylenediisocyanate were charged, heated to 80° C. and allowed to react for ten hours. 24.4 parts of 2-hydroxyethyl acrylate and 0.1 part of methoquinone were added and after ten hours of reaction at 80° C., urethane acrylate was obtained.

Synthesis example 2
130 parts of poly(tetramethylen glycol) (molecular weight 650, OH value 172.6), 49.6 parts of ethylene glycol, and 348 parts of tolylenediisocyanate were charged and allowed to react for ten hours at 80° C. Then, 243.6 parts of 2-hydroxyethyl acrylate and 0.4 parts of methoquinone were added and after ten hours of reaction at 80° C., urethane acrylate was obtained.

Examples of (B) (metha)acrylate represented by formula (1)
Example 1
258 parts of a compound represented by formula

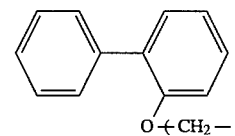

(6)

O—(CH₂—CH₂—O)₂—H (produced by Sanyo Chemical Industries, Ltd., reaction product of 1 mol of o-phenylphenol and 2 mol of ethylene oxide, trade name: Newpol OPE-20, OK value 217.5), 86.5 parts of acrylic acid, 300 parts of toluene, 21 parts of sulfuric acid and 5 parts of hydroquinone were charged and the mixture was heated. The produced water was distilled out together with the solvent, condensed and collected in a separator. When 18 parts of water was collected at the separator, the reaction mixture was cooled. The reaction temperature was 130°–140° C. The reaction mixture was solved in 500 parts of toluene, neutralized by 20% NaOH aqueous solution, and washed three times with 100 parts of 20% NaCl aqueous solution. By distilling off the solvent under reduced pressure, 303 parts of and acrylate represented by formula (7) was obtained.

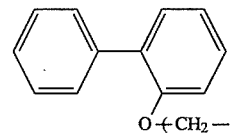

(7)

O—(CH₂—CH₂—O)₂—C(=O)—CH=CH₂

The viscosity (25° C.) was 204 CPS and refractive index (23° C.) was 1.567. The product was almost odorless. The results of high resolution NMR measurement of the product are shown below.

| No. | ppm | No. | ppm |
|---|---|---|---|
| 1 | 166.355 | 24 | 126.976 |
| 2 | 166.116 | 25 | 121.878 |
| 3 | 155.988 | 26 | 121.496 |
| 4 | 155.931 | 27 | 121.433 |
| 5 | 155.601 | 28 | 113.397 |
| 6 | 138.735 | 29 | 113.078 |
| 7 | 138.697 | 30 | 77.6764 |
| 8 | 138.417 | 31 | 77.2515 |
| 9 | 138.476 | 32 | 76.8249 |
| 10 | 131.304 | 33 | 70.9181 |
| 11 | 131.223 | 34 | 70.7309 |
| 12 | 131.176 | 35 | 70.6585 |
| 13 | 131.127 | 36 | 69.7294 |
| 14 | 131.063 | 37 | 69.6619 |
| 15 | 129.814 | 38 | 69.3804 |

| No. | ppm | No. | ppm |
|---|---|---|---|
| 16 | 129.706 | 39 | 69.1516 |
| 17 | 128.775 | 40 | 68.4765 |
| 18 | 128.446 | 41 | 68.4124 |
| 19 | 128.310 | 42 | 66.6048 |
| 20 | 128.089 | 43 | 63.8007 |
| 21 | 128.033 | 44 | 63.7501 |
| 22 | 127.079 | 45 | 62.7957 |
| 23 | 127.035 | 46 | 0.0000 |

The above measurement was done with tetramethylsilane as standard material and deuterochloroform as solvent and by proton decoupling method.

Example 2

346 parts of a compound represented by formula (8)

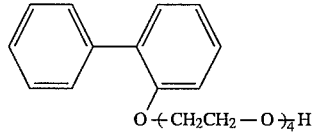

(8)

(produced by Sanyo Chemical Industries, Ltd., reaction product of 1 mol of o-phenylphenol and 4 mol of ethylene oxide, trade name: Newpol OPE-40, OH value 162), 86.5 parts of acrylic acid, 400 parts of toluene, 21 parts of sulfuric acid and 6 parts of hydroquinone were charged and the mixture were heated. The produced water was distilled out together with the solvent, condensed and collected in a separator. When 18 parts of water was collected at the separator, the reaction mixture was cooled. The reaction temperature was 130°–140° C. The reaction mixture was solved in 500 parts of toluene, and 380 parts of an acrylate represented by formula (9) was obtained in the same manner as in Example 1.

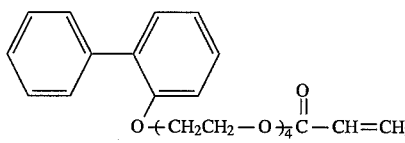

(9)

The viscosity (25° C.) was 120 CPS and refractive index was 1.543. The product was almost odorless.

| Results of NMR measurement | | | |
|---|---|---|---|
| No. | ppm | No. | ppm |
| 1 | 166.357 | 24 | 126.988 |
| 2 | 166.118 | 25 | 121.880 |
| 3 | 155.990 | 26 | 121.498 |
| 4 | 155.933 | 27 | 121.435 |
| 5 | 155.603 | 28 | 113.399 |
| 6 | 138.737 | 29 | 113.080 |
| 7 | 138.698 | 30 | 77.6766 |
| 8 | 138.419 | 31 | 77.2517 |
| 9 | 131.478 | 32 | 76.8281 |
| 10 | 131.306 | 33 | 70.9153 |
| 11 | 131.225 | 34 | 70.7311 |
| 12 | 131.178 | 35 | 70.6587 |
| 13 | 131.129 | 36 | 69.7296 |
| 14 | 131.065 | 37 | 69.6621 |
| 15 | 129.816 | 38 | 69.3806 |
| 16 | 129.706 | 39 | 69.1563 |
| 17 | 128.777 | 40 | 68.4767 |

| Results of NMR measurement | | | |
|---|---|---|---|
| No. | ppm | No. | ppm |
| 18 | 128.448 | 41 | 68.4126 |
| 19 | 128.313 | 42 | 66.6050 |
| 20 | 128.092 | 43 | 63.8009 |
| 21 | 128.035 | 44 | 63.7503 |
| 22 | 127.082 | 45 | 62.7959 |
| 23 | 127.037 | 46 | 0.0000 |

Example 3

214 parts of a compound represented by formula (10),

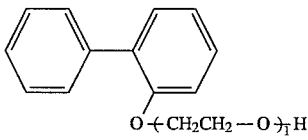

(10)

86.5 parts of acrylic acid, 300 parts of toluene, 21 parts of sulfuric acid and 5 parts of hydroquinone were charged and the reaction was effected in the same manner as in Example 1. The reaction mixture was cooled when 18 parts of water was collected. 257 parts of an acrylate represented by formula (11) was obtained in the same manner as in Example 1.

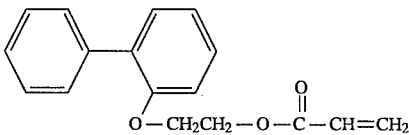

(11)

The viscosity (25° C.) was 127 CPS and refractive index (23° C.) was 1.576. The product was almost odorless.

| Results of NMR measurement | | | |
|---|---|---|---|
| No. | ppm | No. | ppm |
| 1 | 166.144 | 13 | 121.964 |
| 2 | 155.624 | 14 | 121.897 |
| 3 | 138.440 | 15 | 113.405 |
| 4 | 131.498 | 16 | 77.6595 |
| 5 | 131.313 | 17 | 77.2330 |
| 6 | 131.254 | 18 | 76.8080 |
| 7 | 129.731 | 19 | 66.6200 |
| 8 | 128.797 | 20 | 62.8143 |
| 9 | 128.330 | 21 | 59.8314 |
| 10 | 128.245 | 22 | 33.6902 |
| 11 | 128.112 | 23 | 0.0000 |
| 12 | 127.101 | | |

Example 4

241 parts of a compound represented by formula (12),

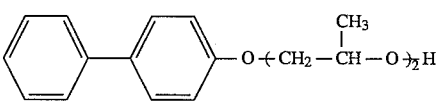

(12)

129 parts of methacrylic acid, 300 parts of toluene, 25 parts of sulfuric acid and 5 parts of hydroquinone was charged and the reaction was carried out in the same manner as in Example 1. The reaction mixture was cooled when 18 parts of water was collected. 316 parts of a methacrylate represented by formula (13) was obtained,

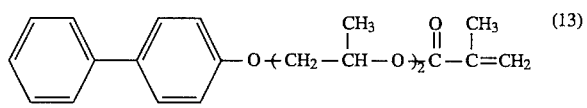

(13)

in the same manner as in Example 1. The viscosity (25° C.) was 190 CPS and refractive index (23° C.) was 1560. The product was almost odorless.

| Results of NMR measurement | | | |
|---|---|---|---|
| No. | ppm | No. | ppm |
| 1 | 167.035 | 23 | 77.2515 |
| 2 | 166.951 | 24 | 76.8249 |
| 3 | 156.551 | 25 | 75.4962 |
| 4 | 156.502 | 26 | 75.4506 |
| 5 | 155.993 | 27 | 75.3056 |
| 6 | 135.244 | 28 | 75.0898 |
| 7 | 135.207 | 29 | 73.5452 |
| 8 | 135.005 | 30 | 73.4508 |
| 9 | 126.775 | 31 | 73.1692 |
| 10 | 126.446 | 32 | 73.0900 |
| 11 | 126.310 | 33 | 71.8978 |
| 12 | 126.089 | 34 | 71.8270 |
| 13 | 126.033 | 35 | 71.6415 |
| 14 | 125.079 | 36 | 70.1880 |
| 15 | 125.036 | 37 | 70.1425 |
| 16 | 124.975 | 38 | 70.0177 |
| 17 | 120.578 | 39 | 18.105 |
| 18 | 120.352 | 40 | 17.2970 |
| 19 | 120.035 | 41 | 17.1604 |
| 20 | 113.397 | 42 | 16.7524 |
| 21 | 113.053 | 43 | 0.0000 |
| 22 | 77.6764 | | |

Applied examples of the resin composite of this invention
Applied Examples 5–11

Ultraviolet-curing resin composites of compositions shown in Table 1 (figures are weight parts) were placed between a Fresnel-lens metal mold and a 2.5 mm thick acrylic resin board (primer layer applied). Fresnel lens were obtained by curing with ultraviolet irradiation.

TABLE 1

| | Applied Example | | | | | | |
|---|---|---|---|---|---|---|---|
| | 5 | 6 | 7 | 8 | 9 | 10 | 11 |
| (A) component | | | | | | | |
| Urethane acrylate obtained by Synthesis Example 1 | 30 | | | 25 | 20 | | 25 |
| Urethane acrylate obtained by Synthesis Example 2 | | 30 | | | 20 | 30 | |
| KAYARAD R-114 *1 | | | 30 | 10 | | | 10 |
| (B) component | | | | | | | |
| Compound obtained by Example 1 | 15 | | | 20 | 15 | | |
| Compound obtained by Example 2 | | 15 | 20 | | | | |
| Compound obtained by Example 3 | | | | | | 35 | 20 |
| Compound obtained by Example 4 | | | | | | | 10 |
| (C) component | | | | | | | |
| KAYARAD R-551 *2 | 45 | 45 | 30 | 30 | 35 | 35 | 33 |
| tribromophenyl methacrylate | 10 | | | 15 | 10 | | |
| tribromophenyloxyethyl acrylate | | 10 | 20 | | | | |
| (D) component | | | | | | | |
| Ilgacure 184 *3 | 3 | 3 | 3 | 3 | 3 | 3 | 3 |
| Release properties | o | o | o | o | o | o | o |
| Shape reproducibility | o | o | o | o | o | o | o |
| Restorability | o | o | Δ | o | o | o | o |
| Refractive index (23° C.) | 1.5740 | 1.5728 | 1.5770 | 1.5752 | 1.5720 | 1.5775 | 1.578 |
| Scratch resistance | oo | oo | o | oo | oo | oo | oo |

Note.
*1 KAYARAD R-114: Produced by Nippon Kayaku Kabushiki Kaisha, epoxy-acrylate of bisphenol A type epoxy resin (produced by Yuka Shell Co., Ltd., Epicoat 828).
*2 KAYARAD R-551: Produced by Nippon Kayaku Kabushiki Kaisha, tetraethoxy-diacrylate of bisphenol A.
*3 Ilgacure 184: Produced by Chiba-Geigy, photopolymerization initiator, 1-hydroxy-cyclohexyl phenyl ketone As is clear from the evaluation results in Table 1, cured products of the resin composites of this invention are superior in mold release property, shape reproducibility, restorability, and scratch resistance, and have high refractive index (23° C.) of 1.57 or above.

The (meth)acrylates of this invention have little odor, high refractive index, and are useful as component of ultraviolet- and/or electron beam-curing resin composites, in particular resin composites for lens (for example, Fresnel lens and lenticular lens).

The resin composites and the cured products of the ultraviolet-curing resin composites for transmission-type screen of this invention have high refractive index and are superior in mold release property, shape reproducibility, restorability and scratch resistance and suitable for transmission type screen.

What is claimed is:

1. A lens material for transmission screen comprising (A) a (meth)acrylate selected from the group consisting of a urethane (meth)acrylate, an epoxy (meth)acrylate, and a combination of a urethane (meth)acrylate and an epoxy (meth)acrylate, (B) a (meth)acrylate represented by formula (2):

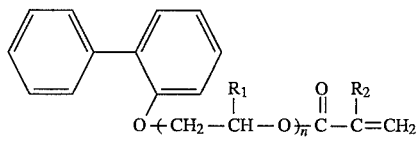

(2)

wherein, $R_1$ and $R_2$ are each independently H or $CH_3$ and average value of n is 1–5; (C) an ethylenically unsaturated compound other than component (A) or (B), and (D) a photopolymerization initiator.

2. A lens material for transmission screen described in claim 1, comprising (A) a (meth)acrylate selected from the group consisting of a urethane (meth)acrylate, an epoxy (meth)acrylate, and a combination of a urethane(meth)acrylate and an epoxy (meth)acrylate, (B) a (meth)acrylate represented by formula (4):

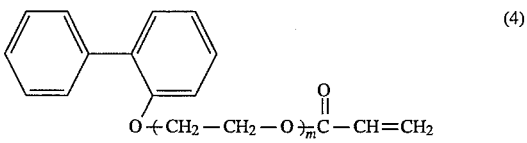

(4)

wherein, average value of m is 1–4; (C) an ethylenically unsaturated compound other than component (A) or (B), and (D) a photopolymerization initiator.

* * * * *